United States Patent [19]
Cloyd

[11] 3,994,296
[45] Nov. 30, 1976

[54] SYRINGE

[75] Inventor: Harold S. Cloyd, Erie, Pa.

[73] Assignee: Nosco Plastics, Inc., Erie, Pa.

[22] Filed: July 25, 1975

[21] Appl. No.: 599,094

Related U.S. Application Data

[60] Division of Ser. No. 279,504, Aug. 10, 1972, which is a division of Ser. No. 98,226, Dec. 15, 1970, Pat. No. 3,766,919, which is a continuation-in-part of Ser. No. 749,448, Aug. 1, 1968, abandoned.

[52] U.S. Cl. .................................................. 128/220
[51] Int. Cl.² ........................................... A61M 5/00
[58] Field of Search ............... 128/220, 221, 218 R, 128/218 P, 218 N, 215

[56] References Cited
UNITED STATES PATENTS

| | | | |
|---|---|---|---|
| 1,770,632 | 7/1930 | Smith | 128/220 |
| 1,848,711 | 3/1932 | Hall | 128/220 |
| 2,478,845 | 8/1949 | Smith | 128/220 |
| 2,551,414 | 5/1951 | Burnside | 128/218 N |
| 2,864,364 | 12/1958 | Mizzy | 128/220 |
| 3,098,482 | 7/1963 | O'Sullivan | 128/220 |
| 3,128,766 | 4/1964 | Mizzy | 128/220 |
| 3,376,866 | 4/1968 | Ogle | 128/272 X |
| 3,543,755 | 12/1970 | Kessel | 128/218 P X |
| 3,870,044 | 3/1975 | Burke et al. | 128/220 |

FOREIGN PATENTS OR APPLICATIONS

| | | | |
|---|---|---|---|
| 162,115 | 12/1953 | Australia | 128/220 |
| 85,146 | 3/1958 | Denmark | 128/218 N |
| 1,441,390 | 11/1968 | Germany | 128/220 |

*Primary Examiner*—John D. Yasko
*Attorney, Agent, or Firm*—Ralph Hammar

[57] ABSTRACT

An inverted type syringe for use with a vial having a stopper piston closing at one end of the vial. Complementary male and female connectors on the upper end of the hub and the adjacent portion of the piston establish a push or pull connection between the piston and the hub. As the connectors are engaged, the piston is punctured so pressure on the vial causes ejection of the contents.

8 Claims, 6 Drawing Figures

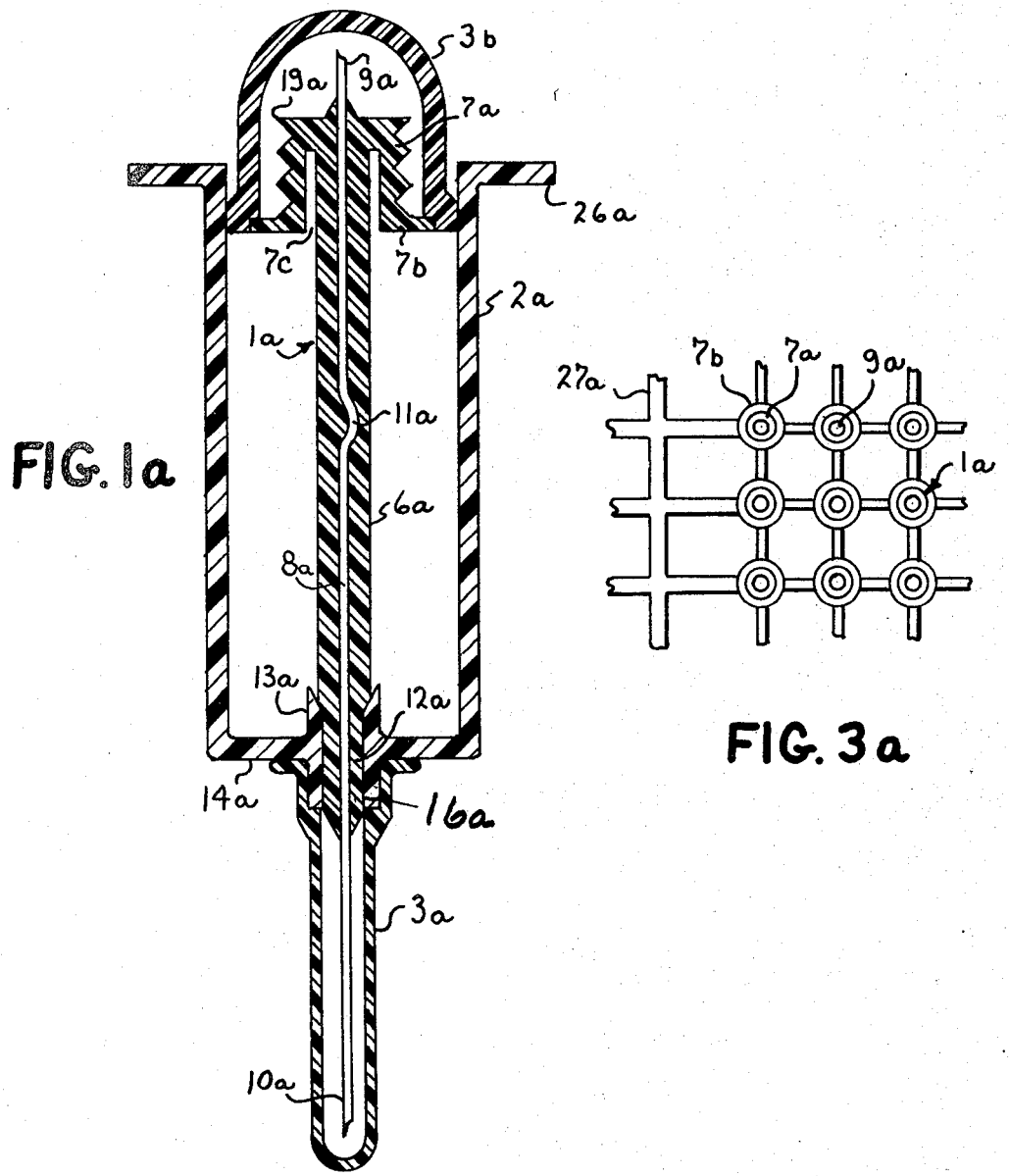

SYRINGE

This is a division of application Ser. No. 279,504, filed Aug. 10, 1972, which is a division of Ser. No. 98,226, filed Dec. 15, 1970, now U.S. Pat. No. 3,766,919 which is a continuation-in-part of application Ser. No. 749,448, filed Aug. 1, 1968, now abandoned, all incorporated by reference.

This invention is intended to simplify the molding of inverted type syringes so the cost can be made low enough for one-time use.

DESCRIPTION OF THE DRAWING

In the drawing,

FIG. 1a, is a sectional view of the syringe as packed for shipment;

FIG. 2a, is a section through the vial for use with the syringe; and

FIG. 3a, is a top plan view of a portion of a tree of molded plastic bodies.

Figure 1:
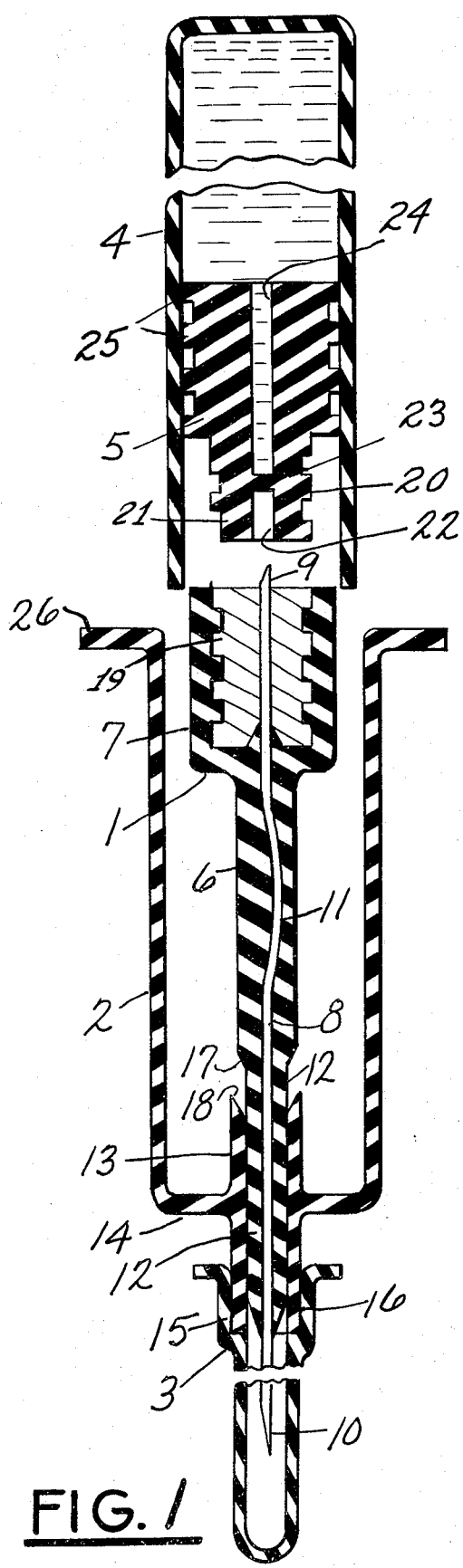
FIG. 1, is a sectional view of the syringe with the parts shown slightly separated.

The syringe consists generally of a thermoplastic body 1 carrying a needle 8, 9, 10, a holder or barrel member 2 enclosing the body, a needle protector 3, and a medicament container vial 4 filled to the required dosage and closed by a pierceable stopper or piston 5 slidably received in the bore of the vial. In use the vial is telescoped into the holder over the body 1 of the syringe structure and the stopper serves as a piston to expel the contents through the needle. At the completion of the injection, the parts are thrown away so it is desirable that each of the parts be as inexpensive as possible.

The body 1 of the syringe structure is injection molded of thermoplastic and comprises an inner tubular member 6 with a socket or female connector 7 at its upper end. A double ended needle 8 is molded into the part 6 and has its upper pointed end or stopper piercing spike 9 near or above the upper end of the socket 7 and has its pointed lower end 10 projecting out the lower end of the inner member 6 so as to be accessible for injection.

In order to hold the needle securely in place an intermediate section of the needle is provided with a bend 11 which anchors the needle within the hub. This is conveniently done by the mold of U.S. Pat. No. 3,330,004 which centralizes the upper and lower ends of the needle while bending the intermediate section. The tubular member 6 has a length substantially equal to the length of the vial so that at the end of the injection operation the vial can be completely telescoped over the member.

Figure 2:
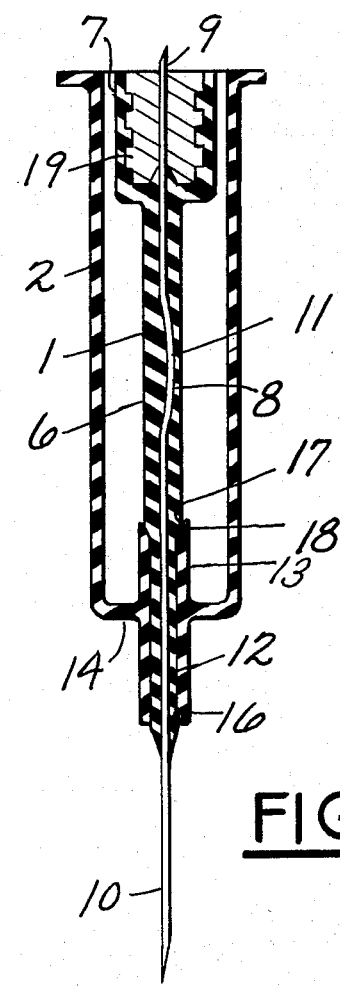
FIG. 2, is a section through the body of the syringe.

The lower end of the member 6 has a reduced section 12 telescoped within a guide sleeve 13 surrounding an aperture extending through the bottom wall or base 14 of the barrel 2 axially inward a distance that is relatively short in relation to the axial extent of the barrel member. The barrel 2 is a separately molded piece of injection molded thermoplastic which is cemented or otherwise sealed or bonded to the reduced section 12 of the member 6. Needle protector 3 is also separately molded and has its upper end 15 in frictional engagement with the projecting lower end 16 of the sleeve 13. In FIG. 1 the needle protector 3 is shown telescoped over the lower end 16 of the sleeve 13 but the body 1 is shown slightly elevated so that a tapered section 17 on the member 6 is spaced above a tapered section 18 on the guide sleeve 13. When in fully assembled position, the body 1 will be lowered into the barrel 2 and the mutually facing tapered sections 17 and 18 will be in engagement as shown in FIG. 2.

The connector or socket 7 has internal threads 19 complementary to and interengaging with the external threads 20 on the reduced projection or connector 21 on the stopper 5. As the lower or open end of vial 4 is telescoped into the holder or barrel member 2, the pointed needle end 9 enters a longitudinal bore 22 in the stopper 5 and the theads 20 on the projection 21 make initial engagement with threads 19 in the socket. Rotation of the vial relative to the holder causes complete engagement of the threads 19 and 20 forces the stopper piercing spike 9 of the needle through a web 23 separating the bore 22 from a bore 24 leading to the upper end of the stopper 5. This establishes communication between the liquid contents of the vial and the pointed upper end 9 of the needle. The parts 7, 21 constituting a telescoping coupling which when engaged or connected establish a push-pull connection for transmitting axial forces in opposite directions. As the vial is pressed downward relative to the barrel or holder 2, the stopper acts as a piston forcing liquid from the vial 4 into the pointed end 9 of the needle and down through the tubular member 6 and through the sleeve 13, 16 and the reduced extension 12 of the tubular member 6 and out through the lower end 10 of the needle. The stopper has external ribs 25 which maintain a seal between the stopper and the inner side walls of the vial while permitting the necessary sliding movement. The holder or barrel 2 has a projecting flange 26 by which the holder may be gripped during injection.

The body 1 of the syringe is molded in a multi-cavity mold in which plastic is injected through a plurality of interconnected runners 27 which feed the plastic into a plurality of locations around the upper edge of each of the sockets or connectors 7. At the end of the molding cycle there is ejected from the mold a tree consisting of a plurality of bodies 1 connected to each other through a tree of runners 27. The tree of molded parts can easily be handled as a unit. All the molded parts will depend from the tree and will be in accurate relation to each other. In order to complete the assembly of the syringe a plurality of needle protectors 3 and holders 2 are assembled into a fixture in which the holders and needle protectors are held in the same spacing as the bodies 1 in the tree 27. The reduced sections 12 and lower ends of the inner members 6 are coated with a solvent and the tree is then lowered so each of the bodies enter its holder. The solvent provides an adhesive coating. As the reduced sections 12 are telescoped within the sleeves 13, 16 of the holders 2, the parts are adhesivably joined in assembled relation. At the end of the assembly each body is joined or bonded to its holder or barrel 2 and each needle is protected by its needle protector. In lieu of the adhesive or solvent, ultrasonic sealing may be used to bond the parts. In this process, ultrasonic vibrarions cause local fusion of the plastic surfaces in contact with each other. After the joint has set up, the tree is broken to separate the individual syringe structures. After appropriate sterilization, each individual syringe structure is ready for use in conjunction with an appropriate vial as described above.

The body 1, holder 2 and needle protector 3 are made in simple molds. The tree 27 holds the molded bodies 1 in positive spacing or alignment so as to permit easy assembly. The plastic to plastic joint between the extension 12 of the tubular member 1 and the sleeve 13, 16 does not require epoxy cements necessary for bonding of metal to plastic. The solvent or cement for the joint is kept away from the needle. Ultrasonic sealing fuses the contacting surfaces without requiring solvent or adhesive. When the projection 21 on stopper 5 is screwed into the socket 7, the vial may be pulled outward to aspirate blood from a vein into the needle to determine that a vein has been punctured.

Figure 3:
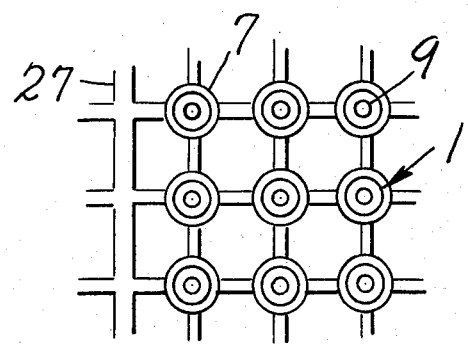
FIG. 3, is a top plan view of a portion of a tree of molded plastic bodies.

The syringe of FIGS. 1a, 2a and 3a consists generally of a body 1a carrying needle 8a, 9a, 10a, a holder or barrel 2a enclosing the body, a needle protector 3a, and a vial 4a filled to the required dosage closed by a stopper or piston 5a slidably received in the bore of th vial. In use the vial is telescoped into the holder or over the body of the syringe and the stopper serves as a piston to expel the contents through the needle. At the completion of the injection, parts are thrown away so it is desirable that each of the parts be as inexpensive as possible.

The body 1a of the syringe is injection molded of thermoplastic and comprises an inner tubular member 6a with a male coupling part 7a at its upper end. At the lower end of the part 7a is an integral flange 7b providing a mounting or sealing surface for a needle cap 3b. A re-entrant recess 7c extends upwardly into the coupling part 7a around the part 6a. A double ended needle 8a is molded into the part 6a and has its upper pointed end 9a above the upper end of the socket 7a and has its pointed end 10a projecting out the lower end of the inner member 6a so as to be accessible for injection.

In order to hold the needle securely in place an intermediate section of the needle is provided with a bend 11a which anchors the needle within the hub. This is conveniently done by the mold of U.S. Pat. No. 3,330,004 which centralizes the upper and lower ends of the needle while bending the intermediate section. The member 6a has a length substantially equal to the vial so that at the end of the injection operation the vial can be completely telescoped over the inner member.

The lower end of the member 6a has a reduced section 12a telescoped within a guide sleeve 13a extending through the bottom wall or base 14a of the barrel 2a, a distance that is relatively short compared to the axial extent of the barrel. The barrel 2a is a separately molded piece of injection molded thermoplastic which is cemented or otherwise sealed or bonded to the reduced section 12a of the member 6a. Needle protector 3a is also separately molded and has its upper end 15a in frictional engagement with the projecting lower end 16a of the sleeve 13a. In FIG. 1a the needle protector 3a is shown telescoped over the lower end 16a of the sleeve 13a.

The connector 7a has external threads 19a complimentary to and interengaging with the internal threads 20a on the connector 21a of the stopper 5. As the lower or open end of vial 4a is telescoped into the open upper end of the holder or barrel 2a, the pointed needle end 9a enters the connector 21a in the stopper 5a and the threads 20a on the connector 21a make initial engagement with threads 19a on the connector 7a. Rotation of the vial relative to the holder causes complete engagement of the threads 19a and 20a and forces the stopper piercing spike 9a of the needle through a web 23a. This establishes communication between the liquid contents of the vial and the pointed upper end 9a of the needle. The parts 7a, 21a constitute a telescoping coupling which when engaged or connected establishes a push-pull connection for transmitting axial forces in opposite directions. As the vial is pressed downward relative to the barrel or holder 2a, the stopper acts as a piston forcing liquid from the vial into the pointed end 9a of the needle and down through the tubular member 1a and through the sleeve 13a, 16a and the extension 12a of the tubular member 1a and out through the lower end 10a of the needle. The stopper has external ribs 25a which maintain a seal between the stopper and the inner side walls of the vial during the necessary sliding movement. The holder or barrel 2a has a projecting flange 26a by which the holder may be gripped during injection.

The body 1a of the syringe is molded in a multi-cavity mold in which plastic is injected through a plurality of interconnected runners 27a which feed the plastic into a plurality of locations around the flanges 7b. At the end of the molding cycle there is ejected from the mold a tree consisting of a plurality of bodies 1a connected to each other through a tree of runners 27a. The tree of molded parts can easily be handled as a unit. All the molded parts will depend from the tree and will be in accurate relation to each other. In order to complete the assembly of the syringe a plurality of needle protectors 3a and holders 2a are assembled into a fixture in which the holders and needle protectors are held in the same spacing as the bodies 1a in the tree 27a. The reduced sections 12a of the needle hubs 6a are coated with a solvent and the tree is then lowered so each of the bodies 1a enters each holder 2a. The solvent provides an adhesive coating. As the reduced sections 12a are telescoped within the sleeves 13a, 16a of the barrels 2a, the parts are joined in assembled relation. At the end of the assembly each body 1a is joined or bonded to its holder 2a and each needle is protected by its needle protector. In lieu of the adhesive or solvent, ultrasonic sealing may be used to bond the parts. In this process, ultrasonic vibrations cause local fusion of the plastic surfaces in contact with each other. After the joint is set up, the tree is broken to separate the individual syringes. After appropriate sterilization, each individual syringe is ready for use in conjunction with an appropriate vial as described above. The body 1a. holder 2a and needle protector 3a are made in simple molds. The tree 27a holds the molded bodies 1a in positive spaced alignment so as to permit easy assembly. The plastic joint between the extension 12a of the tubular member 1a and the sleeve 13a, 16a, does not require an epoxy cement such as necessary for bonding of metal to plastic. The solvent or cement for the joint is kept away from the needle. Ultrasonic sealing fuses the contacting surfaces without requiring solvent or adhesive. When the coupling 7a is screwed into the coupling 21a, the vial may be pulled outward to aspirate into the needle to determine that a vein has been punctured.

I claim:
1. A hypodermic syringe structure for association with a liquid medicament container of the type including a pierceable stopper having a connector thereon, said structure comprising a molded plastic barrel member having an open end, a base opposite said open end having an aperture therethrough and an integral guide sleeve surrounding the aperture in the base and extend- ing axially inwardly of said base a distance that is relatively short in relation to the axial extent of said barrel member, a separately molded plastic inner tubular member having at least a portion thereof fitting within said guide sleeve and an end portion having a connector for coupling engagement with a stopper of such a medicament container, said end portion terminating at the open end of said barrel and having a hollow stopper piercing spike in fluid communication with the inner tubular member, one of said barrel member and inner tubular member having an integral tubular extension projecting outwardly of the aperture in said base, said tubular extension being in fluid communication with the inner tubular member, said barrel member and inner tubular member having mutual facing bonding surfaces, and means effectively bonding said barrel member and tubular member together.

2. A hypodermic syringe structure as claimed in claim 1 and said tubular extension projecting outwardly of said base of said barrel member being integral with said barrel member.

3. A hypodermic syringe structure as claimed in claim 1 and means operatively connected with said projecting tubular extension for receiving a cannula.

4. A hypodermic syringe structure as claimed in claim 1 and said tubular extension projecting outwardly of said base of said barrel member being integral with said tubular member.

5. The hypodermic syringe structure as claimed in claim 1 and said end portion comprising a diametrically enlarged threaded, integrally formed plastic connector portion of said inner tubular member.

6. The hypodermic syringe structure of claim 5 in which said connector is internally threaded.

7. The hypodermic syringe structure of claim 5 and said stopper piercing spike being disposed coaxially with said enlarged threaded portion.

8. The hypodermic syringe structure of claim 7 and said stopper piercing spike being disposed coaxially within said externally threaded porton.

* * * * *